(12) United States Patent
Phillips

(10) Patent No.: US 10,475,270 B2
(45) Date of Patent: Nov. 12, 2019

(54) MINIATURIZED COUNTERFEIT DETECTOR

(71) Applicant: Mesa West, LLC, Las Vegas, NV (US)

(72) Inventor: Robert Phillips, Las Vegas, NV (US)

(73) Assignee: MESA WEST, LLC, Las Vegas, NV (US)

( * ) Notice: Subject to any disclaimer, the term of this patent is extended or adjusted under 35 U.S.C. 154(b) by 74 days.

(21) Appl. No.: 15/817,848

(22) Filed: Nov. 20, 2017

(65) Prior Publication Data

US 2018/0165906 A1 Jun. 14, 2018

Related U.S. Application Data

(60) Provisional application No. 62/432,213, filed on Dec. 9, 2016.

(51) Int. Cl.
*G07D 7/00* (2016.01)
*G07D 7/04* (2016.01)
(Continued)

(52) U.S. Cl.
CPC .............. *G07D 7/003* (2017.05); *G07D 7/00* (2013.01); *G07D 7/04* (2013.01); *G07D 7/12* (2013.01);
(Continued)

(58) Field of Classification Search
CPC ........ G07D 7/00; G07D 7/003; G07D 7/0032; G07D 7/0034; G07D 7/004; G07D 7/0043; G07D 7/0047; G07D 7/04; G07D 7/12; G07D 7/1205; G07D 7/121; G07D 7/128; G01N 21/33; G01N 21/64;
(Continued)

(56) References Cited

U.S. PATENT DOCUMENTS 2,059,197 A * 11/1936 Backer .................. G02B 25/02
356/71
2,161,594 A * 6/1939 Ruth ....................... G07D 7/00
200/52 R
(Continued)

FOREIGN PATENT DOCUMENTS

CN 201322954 Y * 10/2009
DE 10305819 A1 * 9/2004 ............... G07D 7/04
(Continued)

OTHER PUBLICATIONS

Machine translation of TW 265723 U (Year: 2005).*
Machine translation of WO-201132806-A1 (Year: 2011).*
Machine translation of CN-201322954-Y (Year: 2009).*

*Primary Examiner* — Gordon J Stock, Jr.

(74) *Attorney, Agent, or Firm* — Ostrolenk Faber LLP

(57) ABSTRACT

A miniaturized counterfeit detector provides multiple tests to ascertain the authenticity of currency in a rapid fashion. The miniaturized counterfeit detector comprises one or more sensors for magnetic ink testing. One or more backlights, illuminators or both may be provided for visual inspection of watermarks, florescent or other anti-counterfeiting features. The miniaturized counterfeit detector may be fastened to a surface and does not obstruct manipulation of currency to improve testing speed, especially when a number of currency items, such as banknotes or bills, are being tested.

21 Claims, 5 Drawing Sheets

(51) Int. Cl.
*G07D 7/121* (2016.01)
*G07D 7/12* (2016.01)
*G01N 21/64* (2006.01)
*G01N 21/17* (2006.01)
*G01N 21/33* (2006.01)

(52) U.S. Cl.
CPC ............ *G07D 7/121* (2013.01); *G01N 21/33* (2013.01); *G01N 21/64* (2013.01); *G01N 2021/1736* (2013.01); *G01N 2021/1738* (2013.01)

(58) Field of Classification Search
CPC ... G01N 2021/1734; G01N 2021/1736; G01N 2021/1738
USPC ............ 356/71; 250/559.01, 559.04–559.08, 250/559.4, 559.44, 555, 556; 194/205–207, 302, 303, 328
See application file for complete search history.

(56) References Cited

U.S. PATENT DOCUMENTS

| | | | | |
|---|---|---|---|---|
| 3,618,765 A | * | 11/1971 | Cooper | G07D 7/04 209/534 |
| 3,842,281 A | * | 10/1974 | Goodrich | G07D 7/12 250/461.1 |
| 4,187,463 A | * | 2/1980 | Kivenson | G07D 7/04 209/534 |
| 4,558,224 A | * | 12/1985 | Gober | G07D 7/128 250/461.1 |
| D283,803 S | * | 5/1986 | Zonn | D10/46 |
| D368,862 S | * | 4/1996 | Roberts | D10/46 |
| 5,874,742 A | * | 2/1999 | Romano | G01N 21/6447 250/458.1 |
| 5,915,518 A | * | 6/1999 | Hopwood | G07D 7/128 194/207 |
| 5,942,759 A | * | 8/1999 | Romano | G01N 21/6447 250/461.1 |
| 6,590,641 B2 | * | 7/2003 | Yu | G07D 7/12 356/71 |
| 6,795,173 B2 | * | 9/2004 | Romano | G07D 7/128 356/71 |
| D585,311 S | * | 1/2009 | Malhi | D10/46 |
| 7,715,613 B2 | * | 5/2010 | Dobbs | G07D 7/121 356/71 |
| 7,721,965 B2 | * | 5/2010 | Kuo | G06F 1/1616 235/379 |
| D666,514 S | * | 9/2012 | Haas | D10/78 |
| 8,531,652 B2 | * | 9/2013 | Haas | G07D 7/128 356/51 |
| 2005/0259858 A1 | * | 11/2005 | Su | G07D 7/12 382/135 |
| 2010/0000838 A1 | * | 1/2010 | Hamasaki | G07D 7/00 194/207 |
| 2013/0044934 A1 | * | 2/2013 | Tolene | G07D 7/12 382/135 |

FOREIGN PATENT DOCUMENTS

| | | | | |
|---|---|---|---|---|
| KR | 100756032 B1 | * | 9/2007 | ............ G07D 7/128 |
| TW | 265723 U | * | 5/2005 | |
| WO | WO-9630878 A1 | * | 10/1996 | ............ G07D 7/04 |
| WO | WO-03063098 A1 | * | 7/2003 | ............ G07D 7/04 |
| WO | WO-03107281 A1 | * | 12/2003 | ............ G07D 7/04 |
| WO | WO-2011132806 A1 | * | 10/2011 | ............ G07D 7/128 |

* cited by examiner

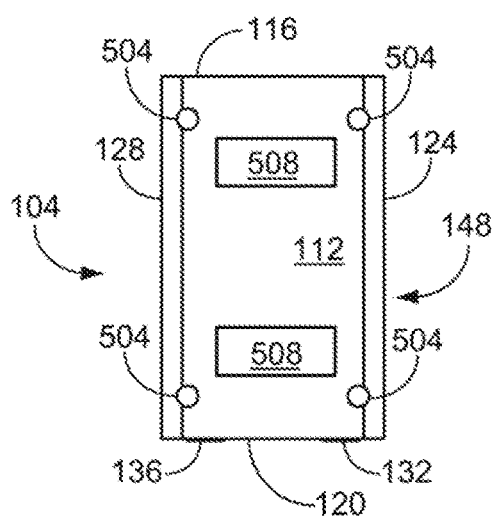
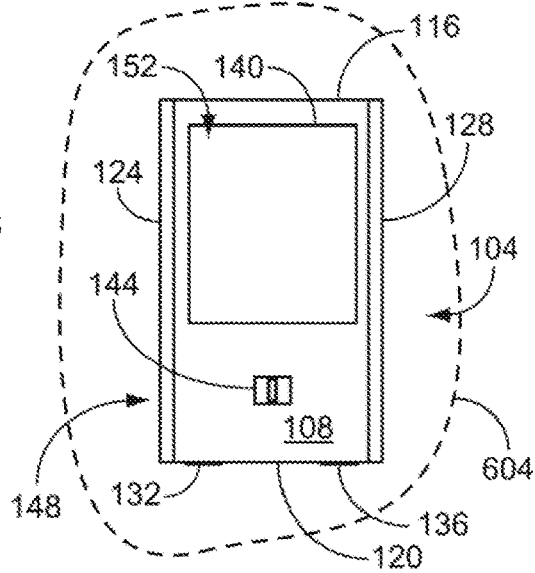
FIG. 5
FIG. 6
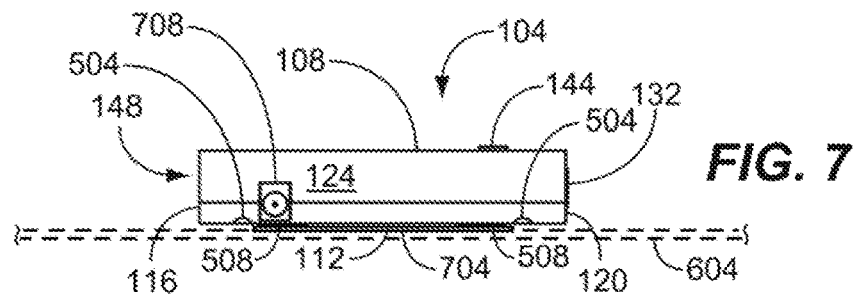
FIG. 7
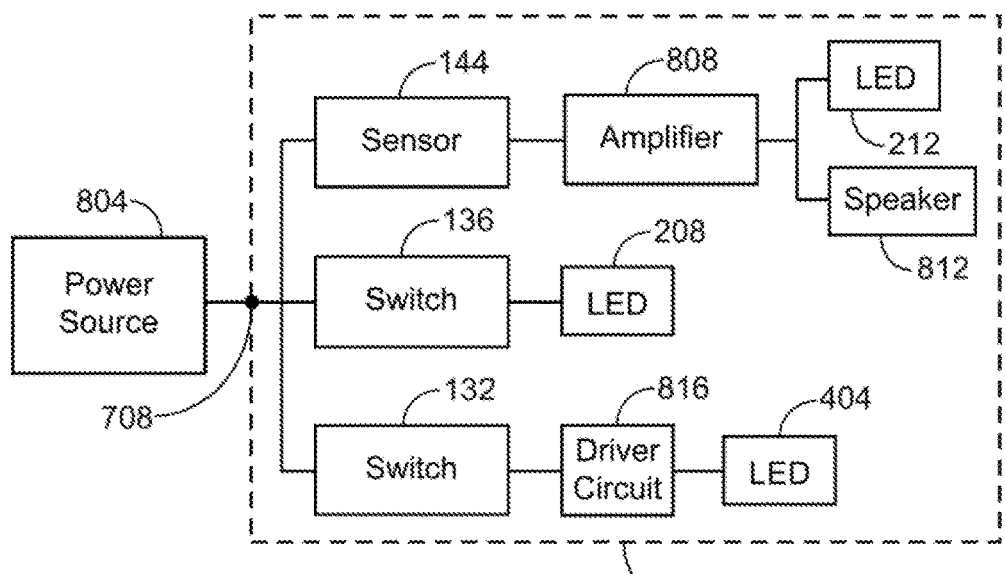
FIG. 8

MINIATURIZED COUNTERFEIT DETECTOR

CROSS-REFERENCE TO RELATED APPLICATIONS

The present application claims the benefit of and priority to U.S. Provisional Patent Application No. 62/432,213, filed Dec. 9, 2016, the entire contents of which are hereby incorporated by reference herein.

BACKGROUND OF THE INVENTION

The present invention relates to counterfeit note or currency detection and, more particularly, to miniaturized counterfeit detectors that easily and rapidly enable carrying out several different tests of the note or currency with hardly at all slowing down cash register operations at stores and similar vendors.

With the use of sophisticated modern printers, counterfeit paper currency is now being made which cannot be detected by visual inspection, even if such inspection is carefully undertaken. Failure to detect counterfeit currency may result in significant losses for individuals or establishments that accept cash. In addition, it is difficult or impossible in some circumstances to accept other forms of payment.

From the discussion that follows, it will become apparent that the present invention addresses the deficiencies associated with the prior art while providing numerous additional advantages and benefits not contemplated or possible with prior art constructions.

The prior art relating to the subject matter of the present invention is extensive and quite crowded, which reflects the persistent, intense and decades long efforts of the prior art to bring to the market truly useable counterfeit detectors that will be widely accepted and deployed at the point of sale by cash register employees in order to stem the flood of counterfeit currency being presented, which ultimately represents a cost that is borne by business establishments.

The prior art is exemplified by the disclosures in U.S. Pat. No. 8,531,655 which describes a three-way desktop UV counterfeit detector and in many other documents including U.S. Pat. Nos. 5,942,759; 659,641; 6,603,871; 6,714,288; 6,795,173; 7,237,711; 7,533,905; 7,715,613; 3,618,765; and United States Patent Application Publication US 2013/0044934. The entire contents of the aforementioned patents and patent publications are incorporated by reference herein.

One of the primary reasons why these types of testers are not deployed more widely at cash registers is due to the fact that space is very tight around cash registers and cash register employees find it difficult to place a large machine or device in that tight area. Moreover, the inspections for counterfeit seem to take up too much time and managers and customers do not like to be subjected to long lines at cash registers. Another factor responsible for the fact that these types of testers are not used universally is that cash register operators usually hold various pieces of papers in their hands and sometimes they only have one hand free to perform counterfeit detection activities.

SUMMARY OF THE INVENTION

Accordingly, it is the general objective of the present invention to provide miniaturized counterfeit detectors that overcome the drawbacks of the prior art.

A miniaturized counterfeit detector for detecting counterfeit currency of various forms is disclosed herein. The miniaturized counterfeit detector provides a miniature, point of sale, multi-test, counterfeit currency detector that may be powered by a plug-in wall adapter. The miniaturized counterfeit detector may detect counterfeit currency by selectively exposing the currency to white light, ultraviolet light, or a magnetic ink sensor for the purpose of detecting various anti-counterfeit features designed into authentic paper currency.

One object of the miniaturized counterfeit detector is to provide a counterfeit currency detector that overcomes the problems of the prior art and to provide a miniature point of sale counterfeit currency detector that has a very small footprint, approximately the size of a pack of cigarettes, which can non-obstructively and conveniently be place next to a standard cash register or point of sale device.

It is also an object of the miniaturized counterfeit detector to provide a triple-test, miniature, point of sale counterfeit currency detector capable of quickly and accurately detecting anti-counterfeit features and properties of authentic currency using white light, ultraviolet light, and a magnetic ink sensor, or various subsets thereof. Diffused white light may be used to detect or distinguish watermarks on authentic currency. Ultraviolet light may be used to detect counterfeit paper and ultraviolet activated features on authentic currency. A magnetic ink sensor may be used to detect the presence of magnetic ink on authentic currency.

Various versions of a miniaturized counterfeit detector and methods therefor are disclosed herein. For instance, in one exemplary embodiment, a miniaturized counterfeit detector comprises a housing having a top and a bottom, one or more backlights at the top, one or more illuminators attached to the housing and one or more controls attached to the housing that activate the backlights and the illuminators. Such miniaturized counterfeit detector also includes one or more magnetic sensors at the top, one or more output devices that generate an output when the magnetic sensors detect magnetic ink and one or more mounts at the bottom.

In preferred embodiments, the invention comprises a miniaturized counterfeit detector for detecting currency or bill counterfeits, the detector including: housing having a top side, and a bottom side for resting on a resting surface; at least one lighting element for providing examination light from the top side of the housing for illuminating currency or a bill being examined; at least one illuminator for providing a special light configured to illuminate an anti-counterfeit feature embedded in the currency of bill; one or more controls coupled to the housing configured to activate the at least one backlight and the at least one illuminator; a magnetic ink sensor coupled to the housing and configured to detect magnetic ink when the currency or bill is wiped against or placed in contact with the magnetic ink sensor by an operator; and at least one output device that generates an output when the magnetic sensor detects magnetic ink.

In preferred embodiments, the special light is UV light configured to visually reveal the anti-counterfeit feature, and a hood is provided extending away from the housing over the at least one illuminator providing the UV light. The hood includes a top wall that is configured as and functions as an awning over the at least one illuminator that blocks the UV light from striking the eyes of the operator and bystanders. Further, the hood extends at an acute angle downwards from the top side toward the bottom side of the housing.

In preferred embodiments, the at least one illuminator is mounted on a front or back wall of the detector, extending vertically between the top side and the bottom side of the detector and the at least one illuminator is configured to cast the UV light at a front or back region on the resting surface located in front or back of the detector where the operator places the currency during a counterfeit test. Further, the magnetic ink sensor is located at the top side of the detector housing, and protrudes from and above a top surface of the housing. Preferably, the housing is rectangular with a length, width and height dimensions measuring less than 115 mm, 75 mm and 35 mm, respectively. Further, a translucent, light diffusing cover extends over the at least one lighting element, the examining light being white light, and the cover is configured to enable the operator to place the currency over it and to visually examine the currency with the white light. The lighting element comprises a plurality of white light LEDs located at the top side of the housing. The white lights are arranged as a matrix of LED lights.

In preferred embodiments, the at least one output device comprises at least one of a colored LED light, a vibration device and a speaker and a circuit for maintaining the output device active steadily or intermittently, for a predetermined time period. The controls comprise one of a white light switch and a white light interrupter which activates the white light LEDs, when one of the switch is activated by the operator and the white light interrupter is activated automatically when the currency is placed on the top side of the housing, the controls also comprise one of a UV light switch and a UV light interrupter which activates the UV light, when one of the switch is activated by the operator and the UV light interrupter is activated automatically when the currency is placed at a location relative to the housing which causes the signal from the UV light interrupter to strike the currency.

In preferred embodiments, an internal battery is located in the housing to power the detector, and/or a power connector is provided for receiving electrical power for the detector from an external power source. Also included is a securing structure configured to hold the detector to the resting surface with sufficient force to prevent the detector from sliding on the resting surface when the operator wipes the currency against the magnetic ink sensor. The securing structure comprises one of a high coefficient friction rubber mat holding the detector in a detector recess in a shape of a foot print of the detector formed therein for contacting the resting surface, double sided sticky tape, hook and loop strips, suction cups and rubberized surfaces.

In preferred embodiments, the method of the invention comprises: providing a counterfeit detection device including: a housing having a top side, and a bottom side for resting on a resting surface; at least one lighting element for providing examination light from the top side of the housing for illuminating currency or a bill being examined; at least one illuminator for providing a special light configured to illuminate an anti-counterfeit feature embedded in the currency of bill; one or more controls coupled to the housing configured to activate the at least one backlight and the at least one illuminator; a magnetic ink sensor coupled to the housing and configured to detect magnetic ink when the currency or bill is wiped against or placed in contact with the magnetic ink sensor by an operator; and at least one output device that generates an output when the magnetic sensor detects magnetic ink; testing the currency by placing the currency on the top side of the detector and examining the currency for the presence of a water mark using white light cast on the currency by the at least one lighting element; rubbing the currency against the magnetic ink sensor and observing whether the output device has generated the output indicating the presence of magnet ink on the currency; and testing the currency by placing it adjacent to the detector housing and observing the currency to determine whether it includes the anti-counterfeit feature which is rendered visible by the special light. The anti-counterfeit feature is a fluorescent strip embedded in the currency.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

Other features and advantages of the present invention will become apparent from the following description of the invention which refers to the accompanying drawings.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views, relative to each embodiment.

FIG. 5 is a bottom view of an exemplary miniaturized counterfeit detector;

FIG. 6 is a top view an exemplary miniaturized counterfeit detector;

FIG. 7 is a side view of an exemplary miniaturized counterfeit detector;

FIG. 8 is a block diagram illustrating components of an exemplary miniaturized counterfeit detector;

DETAILED DESCRIPTION OF EMBODIMENTS OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

Miniature, battery powered, single test counterfeit currency detection devices exist, but are generally not fully reliable and have the added problem of needing frequent battery changes if used on a continuous basis in a 24/7 retail establishment such as a convenience store. Multi-test, desktop sized counterfeit currency detection devices are also known in the prior art but are generally too large and bulky to be conveniently placed at the point of sale in a retail establishment. As a result, counterfeit currency is usually detected by these relatively large desktop devices long after it has been accepted by a retail clerk.

Also, some desktop counterfeit detectors place the UV light source directly over the unit's currency examination area which obstructs the user's view and physically obstructs the currency examination process making the process difficult and time consuming. Consequently, counterfeit testing at the point of sale using a desktop counterfeit detection device is frequently ignored in order to speed up the checkout process and assist impatient customers waiting in line. This problem is exacerbated in the fast-paced convenience store industry where a single money order purchase can sometimes exceed several thousand dollars and the sales clerk simply does not have enough time to properly test numerous bills.

The miniaturized counterfeit detector herein provides a miniature, reliable and unobstructed counterfeit currency detector that can be conveniently located at a point of sale device, such as a cash register, to quickly detect counterfeit currency at the point and time of sale. The miniaturized counterfeit detector may be anchored or attached at or adjacent to a point of sale device to prevent movement during use (thereby increasing efficiency of use), and may be powered by wall power to allow for extended use.

Figure 1:
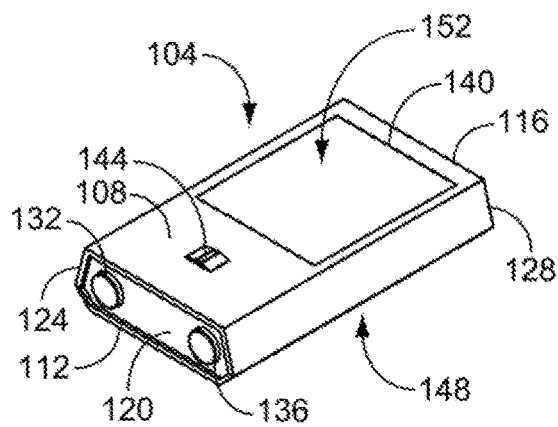
FIG. 1 is a top perspective view of an exemplary miniaturized counterfeit detector.

FIG. 1 illustrates an exemplary miniaturized counterfeit detector 104. A miniaturized counterfeit detector comprises an enclosure or housing 148. A housing may have a top 108, bottom 112, front 116, back 120 and laterally opposed sides 124, 128. In one or more embodiments, a housing 148 may be approximately the size of a pack of cigarettes, on the order of about 85 mm×55 mm×20 mm. This allows the miniaturized counterfeit detector 104 to be used in a wide variety of environments, including environments where space is limited.

One or more sensors 144 may be at a top 108 of a miniaturized counterfeit detector 104. A top 108 may have one or more cut out areas or openings to accommodate one or more sensors 144. This allows the sensors 144 to extend out of the housing 148. Typically, a sensor 144 will be a magnetic sensor that detects the presence of magnetic ink or a magnetic characteristic of currency. In one or more embodiments, a sensor 144 may be a magnetic tape head or the like for example.

One or more backlights 152 may be at a top 108 of a miniaturized counterfeit detector 104 as well. A backlight 152 may comprise a translucent panel 140 that allows light to pass while providing a structure upon which currency may be placed for inspection. It is noted that a transparent panel or translucent panel 140 may be provided in the various embodiments of the miniaturized counterfeit detector 104. Typically, a translucent panel 140 will be provided to provide a diffused light source.

Figure 2:
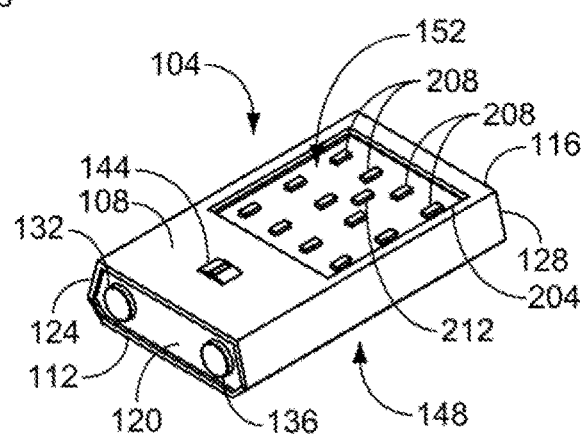
FIG. 2 is a top perspective view of the exemplary miniaturized counterfeit detector of FIG. 1, with the top cover removed.

Referring to FIG. 2, a cut out area or opening 204 may be provided to allow light to be emitted from a miniaturized counterfeit detector 104. An opening 204 may correspond to the shape of the translucent panel 140, such that the translucent panel may be received in the opening 204, such as shown in FIG. 1. It is contemplated that a translucent panel 140 may be attached flush with the exterior surface of the top 108 of a miniaturized counterfeit detector 104 so as to not physically obstruct movement of currency.

A backlight 152 may comprise one or more lighting elements 208 that emit light at a predefined wavelength or wavelengths. A lighting element 208 may be an LED, bulb or other light emitting device. Typically, lighting elements 208 of a backlight 152 will emit white light to illuminate currency placed on the backlight 152 for inspection purposes. As can be seen, a bank or array of lighting elements 208 may be arranged to evenly illuminate a backlight 152.

One or more indicators 212 may also be provided to notify a user when genuine currency has been detected. In the exemplary embodiment of FIG. 2 for example, an indicator 212, in the form of a lighting element, is provided. Typically, an indicator 212 will be activated when genuine currency is detected to alert a user as to the same. It is contemplated that a miniaturized counterfeit detector 104 may be configured to activate one or more indicators 212 when counterfeit currency is detected in some embodiments however.

As stated, an indicator 212 may be a lighting element. In one or more embodiments, such indicator 212 may emit a distinct wavelength or wavelengths of light. For example, a backlight's lighting elements 208 may emit a first wavelength of light while an indicator 212 may emit a second distinct wavelength of light. This allows activation of an indicator 212 to be readily distinguished and noticed by a user. In one or more embodiments, an indicator 212 may be a red lighting element, while a backlight 152 is white.

Various other indicators 212 may be provided in addition or instead of a lighting element as well. Some exemplary indicators 212 include speakers, vibration generators, and other output devices. It is contemplated that all or a subset of a miniaturized counterfeit detector's indicators 212 may be activated simultaneously in one or more embodiments.

An indicator 212 may be secured within a housing 148 of a miniaturized counterfeit detector 104. As shown in FIGS. 1 and 2 for example, the indicator 212 is beneath the translucent panel 140 and emits its light through the translucent panel. It is contemplated that an indicator 212 may be surface mounted or mounted at one or more openings of a housing 148 as well.

Figure 3:
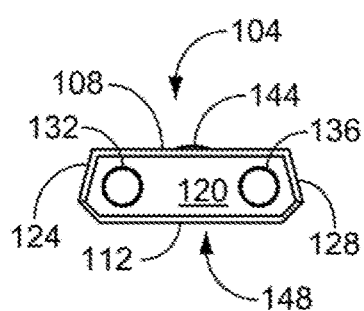
FIG. 3 is a back view of an exemplary miniaturized counterfeit detector.

Referring to FIG. 3, one or more controls 132, 136 may be provided to allow a user to operate various functions of a miniaturized counterfeit detector 104. As can be seen, one or more controls 132, 136 may be mounted to a housing 148 of a miniaturized counterfeit detector 104. In one or more embodiments, one or more controls 132, 136 may be mounted at a back 120 of a housing 148, such as shown in the embodiments of FIGS. 1-3.

Various types of controls 132, 136 may be provided. As shown in FIGS. 1-3 for example, the controls 132, 136 are push button switches that are engaged by pressing them. It is contemplated that a control 132, 136 may be a momentary switch, toggle switch, touch sensor, rocker switch (such as a single pole double throw rocker switch) or the like.

Figure 4:
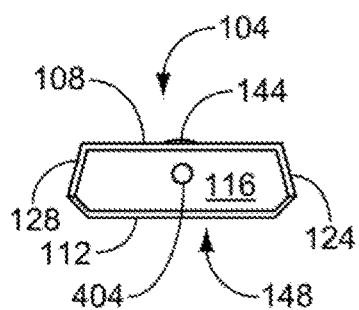
FIG. 4 is a front view of an exemplary miniaturized counterfeit detector.

In operation, a control 132, 136 may be engaged to activate a function of the miniaturized counterfeit detector 104, such as activation of lighting elements 208 of a backlight 152 as shown in FIGS. 1 and 2, or activation of one or more florescent or other anti-counterfeit feature illuminators 404 as shown in FIG. 4. Typically, each control 132, 136 will activate a particular associated function. For example, engaging a first control 136 may activate a backlight 152, while engaging a second control 132 activates an illuminator 404. As another example, one single pole double throw rocker switch may be used to activate both a backlight 152 or illuminator 404, such as by engaging different ends or areas of the switch.

An illuminator 404, when activated, will typically emit light of a particular wavelength to make florescent or other anti-counterfeiting features readily visible to a user. An illuminator 404 will typically emit light of a wavelength that is distinct from that of a miniaturized counterfeit detector's one or more backlights 152 or indicators 212. For example, an illuminator 404 may emit ultraviolet light in one or more embodiments. It is contemplated that an illuminator 404 may emit non-visible wavelengths, such as radio frequency or infrared signals, the reflection of which may be measured to detect counterfeit currency.

As can be seen, one or more illuminators 404 may be at a front 116 of a miniaturized counterfeit detector's housing 148. This allows an illuminator 404 to safely project ultraviolet light away from a user's eyes. In addition, since an illuminator 404 may be at a different area of a housing 148, a view and use of a backlight 152 or sensor 144 is not obstructed.

FIG. 5 illustrates a bottom view of an exemplary miniaturized counterfeit detector 104. As can be seen, in some embodiments, various portions of a housing 148 may be secured together with one or more fasteners 504. Some exemplary fasteners 504 include screws, pins, clips, adhesive and the like. It is contemplated that a housing 148 may also or alternatively be secured together with a friction fit or welds.

In general, a miniaturized counterfeit detector 104 will be placed with its bottom 112 on a surface, such as a counter, table or other support, during operation. It is contemplated that a bottom 112 of a housing 148 may comprise one or more mounts 508 that permanently or temporarily secure the housing to the surface upon which it is placed for use.

Some exemplary mounts 508 include screws, pins and magnets. In the exemplary embodiment of FIG. 5, the mounts 508 are shown as strips, which may be hook and loop fasteners, or tape. A corresponding mount, such as a mating strip of hook and loop fastener, a threaded or other opening or magnetic material, if needed may be installed at the surface upon which a miniaturized counterfeit detector 104 is to be placed. It is contemplated that a receptacle may be at the housing 148, while a mount is at the surface instead, in some embodiments. Some additional exemplary mounts 508 include double sided mounting tape, suction cups, rubberized surfaces, adhesive or welds.

Attachment to a surface allows a miniaturized counterfeit detector 104 to be more easily and efficiently used by preventing its movement during use. In addition, a user's hands are freed from holding the miniaturized counterfeit detector 104 in place when in use. This allows a user to more easily manipulate currency relative to a miniaturized counterfeit detector 104 to detect counterfeits. FIGS. 6 and 7 illustrate an exemplary surface 604 upon which a miniaturized counterfeit detector 104 may be placed. In the exemplary embodiment of FIG. 7, it can be seen that one or more mounts 508 and their corresponding mounts 704 (e.g., mating strips of hook and loop fasteners) may engage one another to secure or attach a miniaturized counterfeit detector 104 to a surface 604.

FIG. 7 also illustrates a power jack or input 708 through which electrical power may be received by a miniaturized counterfeit detector 104. Various power sources may be attached to an input 708 to power a miniaturized counterfeit detector 104. Typically, power from a wall outlet will be used to ensure a miniaturized counterfeit detector 104 may be used for extended periods of time. If needed, a power adapter may be utilized to provide desired voltage and current, such as a 120VAC to 12VDC power adapter. It is contemplated that a miniaturized counterfeit detector 104 may include its own power source, such as a battery, in some embodiments. A power source may be internal or external to a miniaturized counterfeit detector's housing 148.

As can be seen, an input 708 may be at its own side 124 of a housing 148 so as to not obstruct use of one or more controls 132, sensors 144, lighting elements or illuminators when a miniaturized counterfeit detector 104 is connected to a power source at the input.

Operation of an exemplary miniaturized counterfeit detector 104 will now be described. As stated, a miniaturized counterfeit detector 104 may be powered by the use of a standard 120VAC input to 12VDC output wall adapter or other power source plugged into a power input 708, as shown in FIG. 7. After power up, three tests, or a subset thereof, may be performed on a currency item, such as a bill, banknote or other currency. The tests may be performed in the sequence disclosed below or as desired by a user.

A first test involves rubbing the face of a currency item against a sensor 144, such as shown in FIGS. 1 and 2. The black (or other) ink on the face of U.S. banknotes and most foreign banknotes is magnetic. When the face of an authentic currency item is slid or rubbed against the sensor 144, the sensor detects the magnetic ink thereof, and one or more indicators 212, such as one or more lighting elements, speakers, other output or a subset thereof, are activated. For example, an indicator may flash, emit an audible alarm or both. This notifies the user that the currency is authentic.

As can be seen from FIG. 7, if attached to its supporting surface 604, a miniaturized counterfeit detector 104 is held in place while a user slides or rubs a currency item across the sensor 144. This allows a user to rapidly test a number of currency items, as both the user's hands are free to separate and manipulate individual currency items for testing. In addition, the backlight 152 of a top 108 of a miniaturized counterfeit detector 104 may be flush with its housing 148 to permit testing of currency items without currency items becoming caught or obstructed by physical structures at the top as they are slid or rubbed across a sensor 144. As can be seen, a sensor 144 may protrude outward from the top 108 to allow a currency item to readily engage the sensor.

A second test uses diffused white light from a backlight 152 to backlight a currency item in order to reveal watermarks that are contained in all authentic U.S. banknotes and most foreign banknotes. For this test, a currency item is placed over the translucent panel 140 of a backlight 152, such as that shown in FIG. 6. A control 136, which may normally be in an off position, may be depressed or otherwise engaged, to power and activate one or more lighting elements 208, such as shown in FIG. 2, located below the translucent panel 140 which illuminates the backlight 152. The backlight 152 illuminates the currency item revealing any watermarks of the currency item. If watermarks are present or the proper watermarks are present the currency item may be deemed authentic.

A third test involves illuminating a currency item with an illuminator 404 of a miniaturized counterfeit detector 104, such as that shown in FIG. 4. As stated, such illumination will typically be an ultraviolet wavelength. U.S. banknotes except for the one dollar bill and most foreign currencies have ultraviolet activated anti-counterfeit features. For this test, a currency item is placed in front of the illuminator 404 and a control 132 is depressed or otherwise engaged to activate the illuminator. This powers the illuminator 404 which illuminates the currency item with ultraviolet light. This in turn activates any florescent anti-counterfeit features present in the currency item. In general, authentic currency will include florescent anti-counterfeit features while counterfeit currency will be illuminated a bright blue color.

FIG. 8 illustrates components of an exemplary miniaturized counterfeit detector 104. As can be seen, a miniaturized counterfeit detector 104 may have one or more circuits for its various functions. As shown in FIG. 8 for example, the miniaturized counterfeit detector 104 comprises separate circuits for each of the three tests disclosed above. It is contemplated that, in some embodiments, only a subset of the testing capabilities and circuits or components may be provided. In addition, the components of a miniaturized counterfeit detector 104 may be provided in various combinations or arrangements that provide the functionality disclosed herein.

A first circuit may comprise a sensor 144, an amplifier 808 and an output device, such as the indicator 212, speaker 812 or both shown in FIG. 8. An amplifier 808 may be an integrated circuit, controller, router or other component. When a sensor 144 detects magnetic ink, a signal of the same is received at the amplifier 808, which activates an output device, such as the indicator 212, speaker 812 or both. This notifies a user that the currency item at the sensor 144 contains magnetic ink and is likely authentic. If magnetic ink is not detected by the sensor 144, no output is provided.

A second circuit comprises a control 136 and one or more lighting elements 208 of a backlight. When the control 136 is engaged, the circuit is closed and the lighting elements 208 are illuminated. This backlights a currency item, as described above. The lighting elements 208 may be deactivated by disengaging the control 136, in the case that the control is a momentary switch. Alternatively, the control 136 may be toggled or engaged again to deactivate the lighting elements 208, such as if the control 136 is a toggle or other switch.

A third circuit comprises a control 132 and one or more illuminators 404. When the control 132 is engaged, the illuminators 404 are illuminated. A user may then verify the presence and contents of any florescent or other anti-counterfeiting features of a currency item being tested, such as disclosed above. The illuminators 404 may be deactivated by releasing or disengaging the control 132 or by toggling or engaging the control again, such as disclosed above.

Certain illuminators 404, such as UV LEDs, may require precise voltage to prevent overheating or melting and ensure proper operation. In one or more embodiments, a driver circuit 816 may be provided to control or regulate voltage output to an illuminator 404. As shown in the exemplary embodiment of FIG. 8 for instance, a driver circuit 816 is provided between a control 132 and illuminator 404.

A driver circuit 816 may be a voltage regulator or the like, and may also regulate current in one or more embodiments. In addition, it is contemplated that an additional driver circuit may optionally be provided for one or more lighting elements 208. In such case, a second driver circuit may be installed between a control 136 and a lighting element 208 to regulate the voltage (or current) to the lighting element 208.

As can be seen, the circuits may be connected to one or more power sources 804 and powered by the same, such as via one or more power jacks or inputs 708. As disclosed above, a power source 804 may be external to a miniaturized counterfeit detector 104, such as shown. A power source 804 may also or alternatively be internal to a miniaturized counterfeit detector 104, such as a battery, solar panel or other power source, attached to or supported by the miniaturized counterfeit detector's housing.

It is noted that counterfeit currency will typically fail the magnetic ink test provided by the sensor 144. Because of this, most counterfeit currency testing may be limited to the magnetic ink test since the same can be performed quickly on a number of currency items. For example, when a sales clerk collects a banknote as payment, they can quickly slide the face of the banknote over the sensor 144 before placing the banknote in a cash register till. This may take less than a second to perform. Therefore, a stack of banknotes received for a large purchase can be tested in a matter of seconds. To illustrate, a trained clerk can test five hundred dollars in twenty dollar bills in less than twenty seconds.

As described above, the counterfeit detector of the present invention provides a multi-test counterfeit detection capability in an exceedingly small and miniaturized package, on the order of a size of a package of cigarettes which represents a counterintuitive solution because typically devices of this type need to be heavy and sturdy so that they do not slide when placed on a desktop surface, for example near a point of sale cash register surface.

Reference is now made to FIGS. 9-16, which relate to a variant of the above-described embodiment of the present invention. In this variant of the invention, the two push button switches 132, 136, which turn on the LEDs have been eliminated and replaced with photo interrupter sensors (describe below) that switch on either the UV or white light LEDs when a bill is placed over the white light examination area or near the UV LEDs. This enables all three counterfeit tests to be performed quickly using only one hand. When the bill is removed, the lights turn off. A time out feature has been incorporated into both sensor circuits so that the LEDs automatically turn off after about 20 seconds if a bill or object is unintentionally left near either sensor.

In this variant embodiment, an on/off switch (described below) has been added to the front of the device to turn on or off the speaker for the magnetic ink test. Since the audible noise for the magnetic ink test may be offensive to some customers in higher end, quiet locations, this additional feature addresses that concern. The power jack has been moved from the side of the device to the front. Also, this variant of the device employs multiple UV LEDs, preferably two and these UV LEDs have been placed at the back of the device, facing the cash register operator and a hood or shroud has been placed over the LEDs to protect the operator's eyes from being exposed accidentally to the UV light. The UV LEDs have also been angled downward, preferably by about 20 degrees to direct the UV light downward away from anyone's eyes. Lastly, recessed spaces have been molded into the bottom of the device to accommodate double sided stick tape or hook and loop tape used for securing the device to its resting surface. This allows the unit to sit almost flush with the resting surface.

Figure 9:
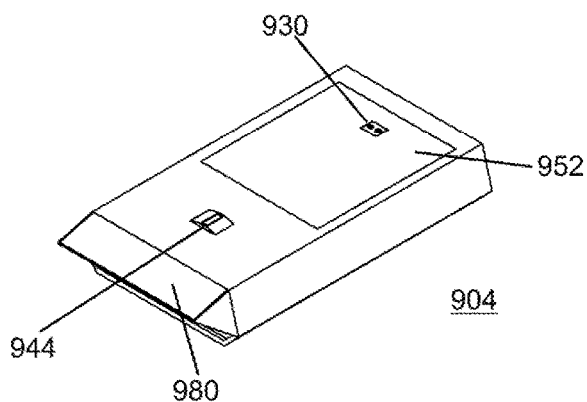
FIG. 9 is a top perspective view of a further, variant exemplary miniaturized detector.

The counterfeit detector 904 shown in FIG. 9 has substantially the same features as the detector 104 in FIG. 1. Thus, for example, it includes a magnetic test sensor 944 corresponding to the magnetic sensor 144 in FIG. 1. But in departure from the embodiment of FIG. 1, the FIG. 9 embodiment includes a reflective photo interrupter sensor 930 which is used to turn on the white light LEDs 982 for watermark testing, as previously described. That feature provides a facility for automatic initiation of the test when a currency note is placed over the translucent cover 952.

In addition, the ultraviolet light source referred to as the light source 404 in FIG. 4 is now provided in the form of a pair of UV LEDs 1104a and 1104b that are located under a hood 980, facing the operator. The light of the UV LEDs is directed downward toward the surface on which the detector 904 is resting, at an acute angle. The hood 980 slopes at an angle over the UV LEDs to shield the operator's eyes from the UV light which points downward.

Figure 10:
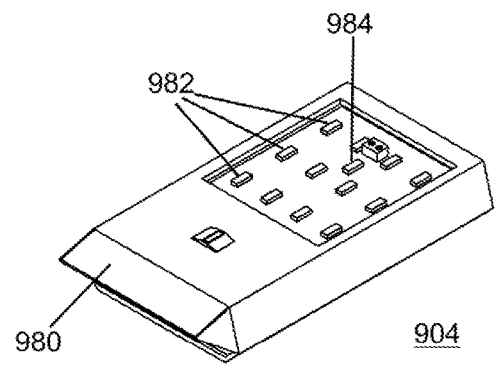
FIG. 10 is a top perspective view of the variant exemplary miniaturized counterfeit detector of FIG. 9, with the top cover removed.

As shown in FIG. 10, the bank of white light LEDs 982 are arranged in several rows on the surface of the detector 904, typically under the cover 952 (FIG. 9). The magnetic ink test green light LED 984 is located among the same bank of lights. It functions to provide an indication that the magnetic test has determined that the tested currency is not counterfeit.

Figure 11:
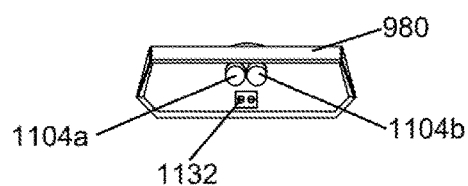
FIG. 11 is a back view of the variant exemplary miniaturized counterfeit detector.
Figure 12:
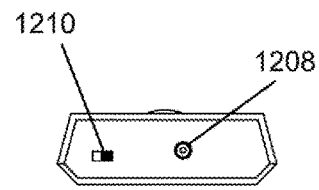
FIG. 12 is a front view of the variant exemplary miniaturized counterfeit detector.

Referring to FIG. 11, the locations of the pair of UV LEDs 1104a and 1104b under the hood 980 is shown, also depicting a reflective photo interrupter 1132 whose function is to turn on the UV LEDs 1104 when a currency or any object is placed at a location close to the hood 980 and the UV lights. The operator need merely observe the features being illuminated by the UV light, for example an internal strip sensitive to UV light that is inside the note or currency being tested. In FIG. 12, the opposed end of view of the detector 904 is shown including a power input connector 1208 and the on/off switch 1210. The switch 1210 functions to turn off a buzzer or speaker 812 (FIG. 16), at the option of the operator.

Figure 13:
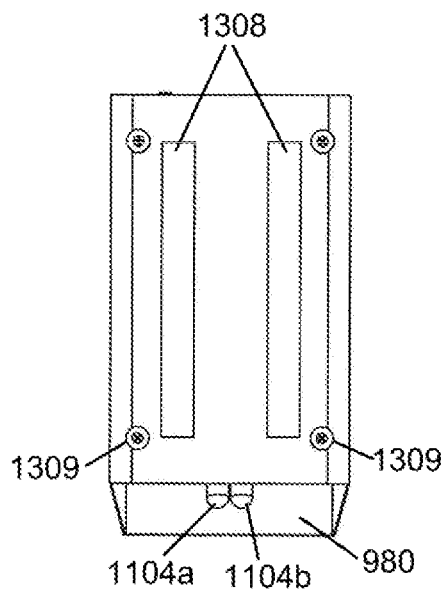
FIG. 13 is a bottom view of the variant exemplary miniaturized counterfeit detector.
Figure 14:
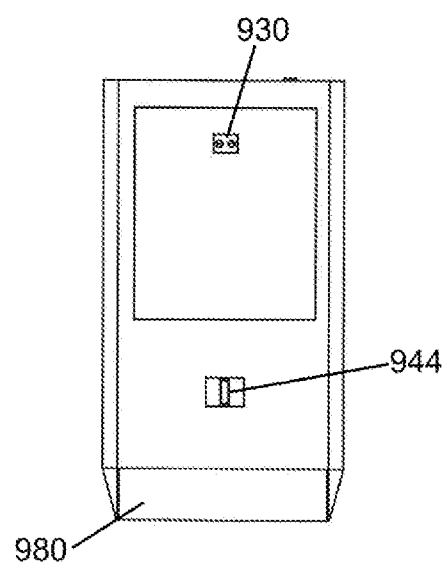
FIG. 14 is a top view of the variant exemplary miniaturized counterfeit detector showing additional features.
Figure 15:
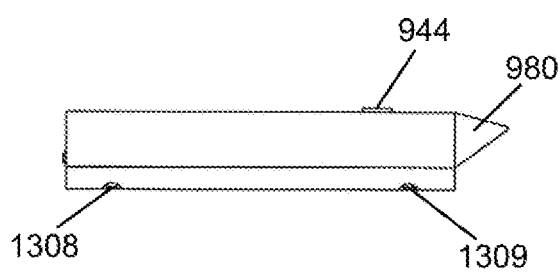
FIG. 15 is a side view of the variant exemplary miniaturized counterfeit detector.

Referring to FIG. 13, at the bottom surface of the detector 904, double sided stick tape 1308 is adhered to the bottom surface, which enables the detector 904 to solidly adhere to the surface on which it is placed. Screws 1309 keep a bottom cover of the device 904 secured in place. If desired, at the location of the double sided tape 1308, the bottom surface is countersunk, producing recesses that allow either the double sided stick tape 1308 or hook and loop material to be placed inside the countersunk recesses so that when the device 940 is placed in its resting place it lies flush with it, as previously noted. In an alternative embodiment, the invention provides a thin, e.g. 3 to 5 mm, rubber mat, dimensionally at least twice or three times larger than the foot print of the detectors 404, 904, with the center of the mat carved out for the detector to fit closely therein, to prevent the detector from sliding when the operator rubs currency against the ink sensor 944. FIGS. 14 and 15 show the detector 904 from a top view and a side view thereof.

Figure 16:
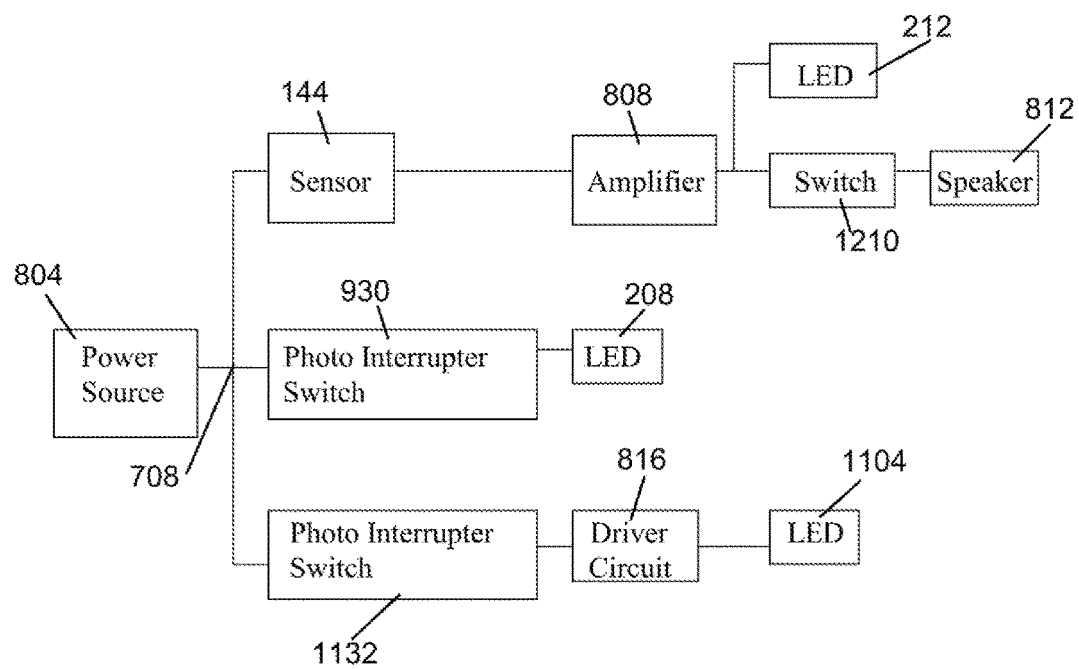
FIG. 16 is a block diagram illustrating components of the variant exemplary miniaturized counterfeit detector.

FIG. 16 is a circuit diagram for the embodiment of FIGS. 9 through 15, and its components are similar to those of FIG. 8. However, in FIG. 16 photo interrupter switches 930 and 1132 have been substituted for the manual switches 136 and 132, respectively. This results in the LED 208 and/or the driver circuit 816 (for the UV LEDs 1104) being turned on automatically, rather than manually, as described above. This speeds up and simplifies usage of the device 904, including by enabling one handed operation. And the speaker 812 can be disabled by the operator by turning off the switch 1210, as also explained above.

If a bill should fail a magnetic ink test, then a backlight test, ultraviolet illuminator test or both can subsequently be performed to confirm that a currency item is counterfeit. This is important since it provides three separate and distinct tests to confirm that a currency item is indeed counterfeit. Also, an illuminator 404 can also be used to verify authenticity of passports and many state and federal identification cards. If desired, such as to reduce wait times while testing currency items, a user may forgo the other tests if a currency item passes a magnetic ink test (i.e., magnetic ink is detected).

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement. For example, the UV LED lights and the hood can be located in the front rather than in the back. The speaker on/off switch can be located elsewhere on the housing, as can be the power plug. An internal battery can be provided to power the detector.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A miniaturized counterfeit detector for detecting currency or bill counterfeits, the detector comprising:
    a housing having a top side, and a bottom side for resting on a resting surface;
    at least one lighting element for providing examination light from the top side of the housing for illuminating currency or a bill being examined;
    at least one illuminator for providing a special light configured to illuminate an anti-counterfeit feature embedded in the currency of bill;
    one or more controls coupled to the housing configured to activate the at least one backlight and the at least one illuminator;
    a magnetic ink sensor coupled to the housing and configured to detect magnetic ink when the currency or bill is wiped against or placed in contact with the magnetic ink sensor by an operator; and
    at least one output device that generates an output when the magnetic sensor detects magnetic ink, and
    wherein the at least one lighting element comprises a plurality of white light LEDs located at the top side of the housing.

2. The counterfeit detector of claim 1, wherein the magnetic ink sensor is located at the top side of the detector housing, and protrudes from and above a top surface of the housing.

3. The counterfeit detector of claim 1, wherein the housing is rectangular with a length, width and height dimensions measuring less than 115 mm, 75 mm and 35 mm, respectively.

4. The counterfeit detector of claim 1, wherein the plurality of white lights are arranged as a matrix of LED lights.

5. The counterfeit detector of claim 1, wherein the one or more controls comprise one of a white light switch and a white light interrupter which activates the white light LEDs, when one of the switch is activated by the operator and the white light interrupter is activated automatically when the currency is placed on the top side of the housing.

6. The counterfeit detector of claim 1, including an internal battery located in the housing to power the detector.

7. The counterfeit detector of claim 1, including a power connector for receiving electrical power for the detector from an external power source.

8. The counterfeit detector of claim 1, wherein the at least one output device comprises at least one of a colored LED light, a vibration device and a speaker.

9. The counterfeit detector of claim 8, including a circuit for maintaining the output device active steadily or intermittently for a predetermined time period.

10. The counterfeit detector of claim 1, including a securing structure configured to hold the detector to the resting surface with sufficient force to prevent the detector from sliding on the resting surface when the operator wipes the currency against the magnetic ink sensor.

11. The counterfeit detector of claim 10, wherein the securing structure comprises one of a high coefficient friction rubber mat holding the detector in a detector recess in a shape of a foot print of the detector formed therein for contacting the resting surface, double sided sticky tape, hook and loop strips, suction cups and rubberized surfaces.

12. The counterfeit detector of claim 1, wherein the special light is UV light configured to visually reveal the anti-counterfeit feature.

13. The counterfeit detector of claim 12, including a hood extending away from the housing over the at least one illuminator providing the UV light.

14. The counterfeit detector of claim 12, wherein the one or more controls comprise one of a UV light switch and a UV light interrupter which activates the UV light, when one of the switch is activated by the operator and the UV light interrupter is activated automatically when the currency is placed at a location relative to the housing which causes the signal from the UV light interrupter to strike the currency.

15. The counterfeit detector of claim 13, wherein the hood includes a top wall that is configured as and functions as an awning over the at least one illuminator that blocks the UV light from striking the eyes of the operator and bystanders.

16. The counterfeit detector of claim 15, wherein the hood extends at an acute angle downwards from the top side toward the bottom side of the housing.

17. The counterfeit detector of claim 16, wherein the at least one illuminator is mounted on a front wall of the detector, extending vertically between the top side and the bottom side of the detector and the at least one illuminator is configured to cast the UV light at a front region on the resting surface located in front of the detector where the operator places the currency during a counterfeit test.

18. The counterfeit detector of claim 16, wherein the at least one illuminator is mounted on a back wall of the detector, extending vertically between the top side and the bottom side of the detector and the at least one illuminator is configured to cast the UV light at a back region on the resting surface located in back of the detector where the operator places the currency during a counterfeit test.

19. A miniaturized counterfeit detector for detecting currency or bill counterfeits, the detector comprising:
 a housing having a top side, and a bottom side for resting on a resting surface;
 at least one lighting element for providing examination light from the top side of the housing for illuminating currency or a bill being examined;
 at least one illuminator for providing a special light configured to illuminate an anti-counterfeit feature embedded in the currency of bill;
 one or more controls coupled to the housing configured to activate the at least one backlight and the at least one illuminator;
 a magnetic ink sensor coupled to the housing and configured to detect magnetic ink when the currency or bill is wiped against or placed in contact with the magnetic ink sensor by an operator;
 at least one output device that generates an output when the magnetic sensor detects magnetic ink; and
 a translucent, light diffusing cover extending over the at least one lighting element, the examining light being white light, and the cover is configured to enable the operator to place the currency over it and to visually examine the currency with the white light.

20. A method for detecting counterfeit currency or bills, the method comprising:
 providing a counterfeit detection device including: a housing having a top side, and a bottom side for resting on a resting surface; at least one lighting element for providing examination light from the top side of the housing for illuminating currency or a bill being examined; at least one illuminator for providing a special light configured to illuminate an anti-counterfeit feature embedded in the currency of bill; one or more controls coupled to the housing configured to activate the at least one backlight and the at least one illuminator; a magnetic ink sensor coupled to the housing and configured to detect magnetic ink when the currency or bill is wiped against or placed in contact with the magnetic ink sensor by an operator; and at least one output device that generates an output when the magnetic sensor detects magnetic ink;
 testing the currency by placing the currency on the top side of the detector and examining the currency for the presence of a water mark using white light cast on the currency by the at least one lighting element;
 rubbing the currency against the magnetic ink sensor and observing whether the output device has generated the output indicating the presence of magnet ink on the currency; and
 testing the currency by placing it adjacent to the detector housing and observing the currency to determine whether it includes the anti-counterfeit feature which is rendered visible by the special light.

21. The method of claim 20, wherein the anti-counterfeit feature is a fluorescent strip embedded in the currency.

* * * * *